United States Patent
Hunt

(10) Patent No.: US 10,584,370 B2
(45) Date of Patent: Mar. 10, 2020

(54) SCREENING FOR L-FORM BACTERIA

(71) Applicant: SOFT CELL BIOLOGICAL RESEARCH, LLC, St. George, UT (US)

(72) Inventor: John Brent Hunt, St. George, UT (US)

(73) Assignee: Soft Cell Biological Research, LLC, St. George, UT (US)

( * ) Notice: Subject to any disclaimer, the term of this patent is extended or adjusted under 35 U.S.C. 154(b) by 124 days.

(21) Appl. No.: 14/969,936

(22) Filed: Dec. 15, 2015

(65) Prior Publication Data

US 2016/0168614 A1    Jun. 16, 2016

Related U.S. Application Data

(60) Provisional application No. 62/209,661, filed on Aug. 25, 2015, provisional application No. 62/165,368, filed on May 22, 2015, provisional application No. 62/155,081, filed on Apr. 30, 2015, provisional application No. 62/092,463, filed on Dec. 16, 2014.

(51) Int. Cl.
*C12Q 1/04*     (2006.01)
*C12Q 1/68*     (2018.01)

(52) U.S. Cl.
CPC ..................... *C12Q 1/68* (2013.01)

(58) Field of Classification Search
None
See application file for complete search history.

(56) References Cited

U.S. PATENT DOCUMENTS

| | | | |
|---|---|---|---|
| 3,936,355 A | 2/1976 | Lawson | |
| 4,610,961 A | 9/1986 | Guardino et al. | |
| 5,135,851 A | 8/1992 | Kajander | |
| 5,672,517 A * | 9/1997 | Domingue | G01N 33/6893 435/7.24 |
| 6,022,730 A | 2/2000 | Robinson | |
| 7,115,385 B2 | 10/2006 | Breitschwerdt et al. | |
| 7,204,637 B2 * | 4/2007 | Sherman | B01F 9/0021 366/214 |
| 7,309,589 B2 * | 12/2007 | Montagnier | C12Q 1/689 435/5 |
| 2001/0036658 A1 | 11/2001 | Phillips et al. | |
| 2004/0198675 A1 | 10/2004 | Sugamata | |
| 2009/0042814 A1 | 2/2009 | Petyaev et al. | |
| 2013/0259845 A1 | 10/2013 | Heidaran et al. | |
| 2013/0323712 A1 | 12/2013 | Sato et al. | |
| 2018/0274005 A1 | 9/2018 | Hunt | |

FOREIGN PATENT DOCUMENTS

| | | |
|---|---|---|
| WO | WO 91/07503 A1 | 5/1991 |
| WO | WO2001066776 | 9/2001 |
| WO | WO 03/046136 A2 | 6/2003 |
| WO | WO 2008/058727 A1 | 5/2008 |
| WO | WO 2016/042041 A1 | 3/2016 |

OTHER PUBLICATIONS

Carolina 3MTM PetrifilmTM Instruction Manual, 2000 pp. 1-12).*
Belsheim et al (Gastroenterology 85:364-9, 1983).*
Glover et al (PLOS One, 4(10):e7316 pp. 1-10).*
Gerhardt et al, Manual of Methods for General Bacteriology, American Society for Microbiology, 1981, pp. 85-88.*
Finegold et al (Diagnostic Microbiology The C.V. Mosby Company 1982, pp. 532-557).*
Pease (Ann. Rhem. Dis. 28:270-274, 1969.*
Dolman et al. "Two Cases of Rat-Bite Fever Due to *Streptobacillus moniliformis*" *Canadian Journal of Public Health*, 1951, vol. 42, pp. 228-241.
Ferguson et al. "An ELISA for the detection of Bacillus subtilis L-form bacteria confirms their symbiosis in strawberry" *Letters in Applied Microbiology*, 2000, vol. 31, pp. 390-394.
Mursic et al. "Formation and Cultivation of Borrelia Burgdorferi Spheroplast-L-Form Variants" *Infection*, 1996, vol. 24, pp. 218-226.
International Search Report and Written Opinion for Application No. PCT/US2015/066102 dated Apr. 8, 2016.
International Preliminary Report on Patentability for Application No. PCT/US2015/066102 dated Jun. 29, 2017.
International Search Report and Written Opinion for Application No. PCT/US2018/034496 dated Aug. 27, 2018.
International Search Report and Written Opinion for Application No. PCT/US2018/044885 dated Oct. 10, 2018.
Supplementary European Search Report for Application No. EP 15870988.1 dated May 23, 2018.
[No Author Listed] 109: Endometriosis, DSU Teaching & Learning Conference/Undergraduate Research Symposium. Apr. 17, 2017. Retrieved from Internet <http://www2.eventsxd.com/event/2551/2017teachinglearningconference/sessions> on Sep. 10, 2018. pp. 1 and 28.
Braundmeier-Fleming et al., Utilizing the Microbiome to Diagnose Endometriosis. Endometriosis Foundation of America. Jul. 4, 2017 Retrieved from Internet: <https://www.endofound.org/utilizing-the-microbiome-to-diagnose-endometriosis> on Sep. 10, 2018. 5 pages.
Kahn et al., Bacterial contamination hypothesis: a new concept in endometriosis. Reprod Med Biol. Jan. 18, 2018;17(2):125-133. doi: 10.1002/rmb2.12083. eCollection Apr. 2018.

(Continued)

*Primary Examiner* — Patricia Duffy

(74) *Attorney, Agent, or Firm* — Wolf, Greenfield & Sacks, P.C.

(57) ABSTRACT

Disclosed herein are methods for screening clinical or biological samples to determine the presence of L-form bacteria within the sample. Methods include contacting a sample to a liquid growth medium and incubating the liquid growth medium at a temperature lower than 37 degrees C. The liquid growth medium is monitored for L-form bacterial growth. An amount of the liquid growth medium is transferred as an inoculant to a solid growth medium, and the solid growth medium is incubated under conditions that maintain a hydrated state of the inoculant to enable the L-form bacteria to efficiently interface with the solid growth medium and continue to grow.

18 Claims, 7 Drawing Sheets

(56) References Cited

OTHER PUBLICATIONS

Kim et al., Intratracheal transplantation of human umbilical cord blood-derived mesenchymal stem cells attenuates *Escherichia coli*-induced acute lung injury in mice. Respir Res. Aug. 15, 2011;12:108. doi: 10.1186/1465-9921-12-108.

Levy et al., Enhancement of neonatal innate defense: effects of adding an N-terminal recombinant fragment of bactericidal/permeability-increasing protein on growth and tumor necrosis factor-inducing activity of gram-negative bacteria tested in neonatal cord blood ex vivo. Infect Immun. Sep. 2000;68(9):5120-5.

Liepke et al., Human hemoglobin-derived peptides exhibit antimicrobial activity: a class of host defense peptides. J Chromatogr B Analyt Technol Biomed Life Sci. Jul. 5, 2003;791(12):345-56.

Yost et al., Neonatal NET-inhibitory factor and related peptides inhibit neutrophil extracellular trap formation. J Clin Invest. Oct. 3, 2016;126(10):3783-3798. doi: 10.1172/JCI83873. Epub Sep. 6, 2016.

* cited by examiner

SCREENING FOR L-FORM BACTERIA

CROSS-REFERENCE TO RELATED APPLICATIONS

This application claims the benefit of U.S. Provisional Patent Application No. 62/092,463, filed Dec. 16, 2014, U.S. Provisional Patent Application No. 62/155,081, filed Apr. 30, 2015, U.S. Provisional Patent Application No. 62/165,368, filed May 22, 2015, and U.S. Provisional Patent Application No. 62/209,661, filed Aug. 25, 2015, the disclosures of each of which are incorporated herein in their entirety.

BACKGROUND

The disclosure relates generally to devices and methods useful for the detection of bacteria, and more specifically to sample collection and preparation devices and methods useful for detecting the presence of L-form bacteria within a sample.

The detection of bacterial infections or bacterial contamination within biological and/or environmental samples is an important endeavor for a wide range of applications, including diagnosis of a disease or condition, determining the appropriateness of surgery for a candidate patient, organ, tissue, or blood donor screening, monitoring infectious diseases within a patient or within a population, and public health planning and information gathering, among others.

L-form bacteria, also referred to as pleomorphic, fastidious, intracellular, or cell-wall-deficient bacteria, are strains of bacteria that are normally known to exist in planktonic form with full cell wall structures, but which lack cell walls and/or reside intracellularly when in L-form. L-forms can develop from Gram-positive as well as Gram-negative bacteria. L-form bacteria are often difficult to detect within clinical samples, and may be missed by standard laboratory procedures. Additionally, L-form bacteria are often more difficult to culture relative to forms having a stable cell wall. Furthermore, because L-form bacteria often survive in the absence of a cell wall or within a host cell, they may have a role in the formation of some types of bacterial antibiotic resistance.

In a typical screening for infection, blood is withdrawn and held at 37° C. for 5-6 days before being plated and analyzed via Gram staining. In a standard lab test, the blood sample is kept in a rocker during the holding period prior to plating of the sample. Unfortunately, these methods often fail to promote the growth of or detect L-form bacteria present in the blood sample, leading to missed diagnoses and improper clearance for implantations or other surgeries.

BRIEF SUMMARY

The present disclosure describes methods that enable the culturing of L-form bacteria found within a sample (e.g., clinical, biological, or environmental). Under particular culture conditions and process steps described herein, L-form bacteria can be successfully cultured and isolated, even in circumstances in which the sample from which the L-form bacteria are cultured is unable to produce any detectable growth using conventional bacterial culturing or infection screening techniques. In addition, certain embodiments have been used to culture bacteria (from an L-form within a sample to a classic-form on solid media) for which no previous reports of successful culture or isolation have been made.

Certain embodiments relate to methods for culturing L-form bacteria, methods for detecting L-form bacteria within a sample, methods for diagnosing a subject as having an infection based on the detection of L-form bacteria within a sample received from the subject, methods for identifying the level, type, or progression of an infection based on the resulting types and levels of bacteria cultured, methods of isolating a bacterial strain from a biological sample containing L-form bacteria, and methods of analyzing a bacterial strain cultured or isolated from a biological sample in order to identify the bacterial strain, harvest the bacterial strain (e.g., for the production of antibodies, vaccines, diagnostic reagents, etc.), and/or test the bacterial strain for antimicrobial sensitivity, antibody sensitivity, or sensitivity to other treatments.

Certain embodiments include contacting a sample to a first growth medium (e.g., a liquid medium), incubating the first growth medium under a first set of incubation conditions, transferring at least a portion of the first growth medium, as an inoculant, to a second growth medium (e.g., a solid medium) under conditions that maintain a hydrated state of the inoculant, incubating the second growth medium under a second set of incubation conditions that maintain a hydrated state of the second growth medium, and monitoring the second growth medium for the presence of bacteria. Certain embodiments include contacting a sample to a first growth medium within a comminuting container, comminuting the sample, incubating the sample under a first set of incubation conditions, and monitoring the first growth medium for the presence of L-form bacteria.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which.

DETAILED DESCRIPTION

Definitions

Figure 1:
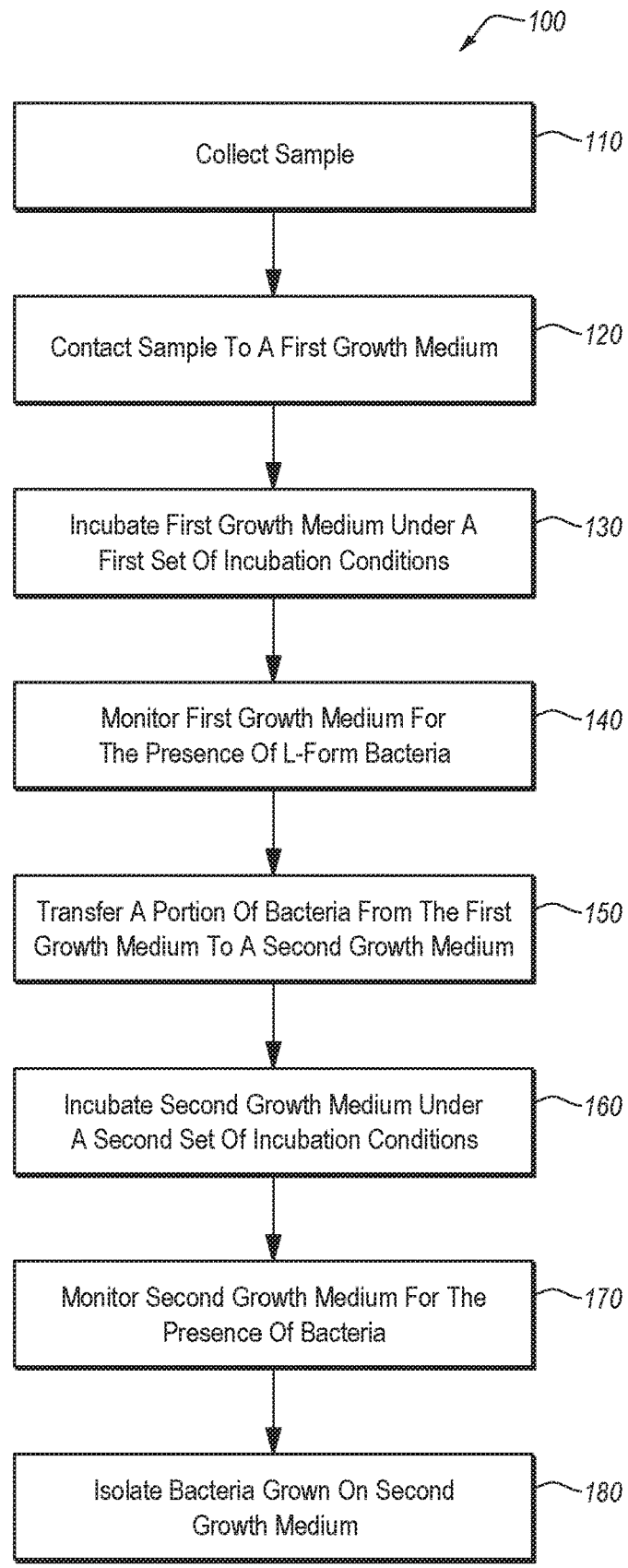
FIG. 1 illustrates an exemplary method for screening a sample for the presence of L-form bacteria.

Embodiments of the present invention are directed toward devices and methods useful in the detection and screening of bacteria within a sample, particularly L-form bacteria within a sample. Many of the embodiments described herein are described with respect to the detection of L-form bacteria. One of skill in the art will note, however, that the devices and methods of the present disclosure are also applicable to the collection, detection, viewing and/or monitoring of other forms of bacterial growth as well.

As used throughout this disclosure the terms "cell-wall-sufficient bacteria" (CWS bacteria) or "classic-form bacteria" refer to strains of bacteria with an identifiable and recognizable cell wall structure, such as the thick peptidoglycan layer of Gram positive bacteria and the thin peptidoglycan layer positioned between the cell membrane and the outer membrane (lipopolysaccharide layer) of Gram negative bacteria. As used herein, the term CWS bacteria also refers to mycobacteria, bacteria within the archaea domain, and other forms of bacteria known to those of skill in the art to typically exhibit a cell wall structure, even if not necessarily easily categorized as Gram positive or Gram negative.

The terms "L-form bacteria," "pleomorphic bacteria," "hidden bacteria," "intracellular bacteria," "fastidious bacteria," and the like do not have standard definitions. The terms are often used synonymously, but in some instances, for example, the term "intracellular bacteria" may refer to bacteria residing within a host cell regardless of level of cell wall formation of the bacteria.

As used herein, the term "L-form bacteria" refers to strains of bacteria residing intracellularly within a host animal cell, strains of bacteria not exhibiting a full cell wall structure, and/or other types of bacteria distinguished from typical planktonic and cell-wall-sufficient bacteria for which traditional culturing and detection methods focus on. "L-form bacteria" include bacterial strains lacking any identifiable cell wall structure or cell wall components, and include strains including an undeveloped or incomplete cell wall structure, such as strains containing some cell wall components but lacking sufficient structure to fully define the cell wall (e.g., strains with variable shape as opposed to typical cocci, rod, and/or spiral characterization).

The term "L-form bacteria" therefore includes strains of bacteria that do not yet include fully recognizable cell wall structures, but which are transitioning toward cell wall sufficient strains. The term "L-form bacteria" also refers to pleomorphic bacteria which are capable of reverting from a classic form to a reduced-cell-wall or absent-cell-wall-form and/or which are capable of progressing from a reduced-cell-wall or absent-cell-wall-form toward a classic form.

Although the exemplary embodiments described herein refer specifically to bacteria, one of skill in the art will understand that the methods, devices, and systems disclosed herein may be utilized for culturing, screening, and/or detecting fungi (e.g., yeast), protozoans, and other pathogenic microorganisms capable of residing intracellularly within host cells and/or capable of hiding from immune system responses within biological fluids or tissues.

Samples used in embodiments of the present invention may include environmental samples and/or biological samples. Biological samples include any sample capable of having a biological material. Specific non-limiting examples include mucus, saliva, feces, blood, serum, plasma, cerebrospinal fluid, urine, or placenta. Biological samples also include biopsies, for example, of skin, dermis, breast, lung, nasopharynx, nose or sinuses, thyroid, head, neck, adrenal gland, thyroid, lymph, gastrointestinal tract, genito-urinary tract, kidney, pancreas, adrenal gland, liver, bone, bone marrow, heart, muscle, or a sample of the hematopoetic system.

In certain embodiments, biological samples may be subjected to a pre-treatment process prior to screening for the presence of L-form bacteria. For example, samples may be comminuted (e.g., blended, ground, vortexed, shredded, sonicated) or otherwise processed and/or may be mixed with other ingredients such as water, saline solution, buffer solution, culture media, or other carrier materials or combinations of ingredients in order to prepare the sample for further screening. In other examples, samples may undergo an extraction procedure to extract desired portions of a sample prior to screening (e.g., to extract certain fluids from a sample or to extract and/or isolate certain cell types, such as white blood cells). In some embodiments, samples may be subjected to one or more disruptive comminution processes to disassociate any biofilms or other aggregates, or to rupture host cells harboring L-form bacteria, or to otherwise disperse any L-form bacteria prior to further screening.

As used herein, "sample" may also refer to mixtures containing an environmental or medical/clinical sample. For example, a sample may be added to or mixed with a growth medium to promote the growth of any bacteria within the sample. When such a mixture is further processed (e.g., transferred, analyzed, monitored, stored, etc.), the mixture may be referred to simply as the "sample."

A "subject" refers to an animal, typically mammalian animals, such as but not limited to humans, non-human primates (apes, gibbons, gorillas, chimpanzees, orangutans, macaques), domestic animals (dogs and cats), farm animals (chickens, turkeys, ducks, horses, cows, goats, sheep, pigs), and experimental animals (mouse, rat, rabbit, guinea pig). Subjects also include animal models, for example, a mouse model of an infection. Subjects include naturally occurring or non-naturally occurring mutated or non-human genetically engineered (e.g., transgenic or knockout) animals. Subjects further include animals having or at risk of having an infection, or having or at risk of having a disease or condition that may be linked or associated with the presence of L-form bacteria. Subjects can be any age. For example, a subject (e.g., human) can be a newborn, infant, toddler, child, teenager, or adult, e.g., 50 years or older or other age.

Subjects include those in need of a method of the disclosure; for example, in need of diagnosis, detection, or screening for the presence of L-form bacteria. A subject is considered to be in need of a device and/or method of the disclosure where it is likely to provide information concerning the presence or absence of L-form bacteria, or is likely to provide information concerning the extent or severity of, the status or prognosis of, or possible treatment or therapy of, a disease or condition linked to or associated with the presence of L-form bacteria within a sample derived from the subject.

Subjects appropriate for screening therefore include those having or at risk of having an infection, or having or at risk of having a disease or condition linked to or associated with L-form bacteria. A subject may therefore be symptomatic or asymptomatic for an infection, disease, or condition. Candidate subjects therefore include subjects that have been exposed to or contacted with an L-form bacteria, or that are at risk of exposure to or contact with an L-form bacteria, regardless of the type, timing or extent of exposure or contact. The disclosed devices and methods are therefore applicable to a subject who is at risk of an L-form bacterial infection, but has not yet been diagnosed with an L-form bacterial infection. Prophylactic methods are therefore included. In one example, subjects that have recently or that are currently undergoing cancer therapy have typically been found not to produce any L-form bacteria. There are also indications of a correlation between L-form bacteria and DNA mutations, suggesting that some L-form bacteria may be a causative agent for cancer.

Additionally, candidate subjects may include, for example, organisms that have an antibiotic resistant bacterial infection, or have been subjected to antibiotics for a period of time and who have or are at risk of developing an antibiotic resistant bacterial infection. Other candidate subjects include, for example, organisms with a condition making them more susceptible to potential infection, such as those with weakened immune systems caused by drug-therapy, cancer treatment, or other conditions affecting the ability to resist infection. Other candidate subjects also include organisms preparing for surgery or other treatment event increasing the risk of infection, such as those preparing for implant surgery (e.g., knee or hip replacement or other surgery including an implantable device).

The term "antibodies" as used herein refers to all types of immunoglobulins, including IgG, IgM, IgA, IgD, and IgE. The antibodies be monoclonal or polyclonal, and may be of any species of origin, including (for example) mouse, rat, rabbit, horse, or human, or may be chimeric antibodies. The antibodies may be recombinant monoclonal antibodies (e.g., produced using a hybridoma cell line).

As used herein, the term "complete antibody" is a subset of "antibodies," and refers to an antibody capable of immunologically interacting with at least one variety (e.g., species, strain) of L-form bacteria, including when the variety is in a cell-wall-deficient state, is residing intracellularly, or is in an L-form state as a result of antibiotic pressure. In contrast, an "incomplete antibody," as used herein, refers to an antibody that is capable of immunologically interacting with at least one variety of bacteria in classic form, but is incapable of immunologically interacting with the same variety when the variety is in an L-form, or is only capable of weak immunological interaction (e.g., at levels insufficient to eradicate an infection) when the variety is in an L-form.

Methods of Screening for L-form Bacteria

FIG. 1 illustrates an exemplary method 100 of screening a sample for the presence of L-form bacteria. In some embodiments, the method includes a step 110 of collecting a sample, a step 120 of contacting the sample to a first growth medium, a step 130 of incubating the inoculated first growth medium under a first set of incubation conditions, and a step 140 of monitoring the inoculated first growth medium for the presence of L-form bacteria.

In some embodiments, the step 110 of collecting the sample is performed using a sample collection device as described herein. In other embodiments, sample collection is performed using standard sample collection techniques, such as a blood draw, tissue swab, and the like. In some embodiments, the sample is collected in the same container in which the first growth medium is contained. Alternatively, the sample may be collected in one or more separate containers prior to storage, transport, and subsequent transfer to the container holding the first growth medium.

In some embodiments, an initial control can be performed by swabbing the skin of a subject (e.g., by swabbing a subject's finger with a cotton swab after sterilizing the finger) and placing the swab in a separate container containing the first growth medium. The control can act as a check against the collected sample in order to reduce or rule out the possibility of contamination of the sample upon detecting the presence of L-form bacteria within the sample. For example, L-form bacteria detected in a blood sample can be compared to bacteria grown from the control, if any. If the type(s) of L-form bacteria identified from the sample are different than the type(s) of bacteria identified from the control, the results suggest that the detected L-form bacteria were not merely the result of skin bacteria contamination of the sample.

Various types and/or combinations of growth media may be used as the first growth medium. For example, the first growth medium may be formulated as complex growth media (e.g., blood, yeast extract, bile, peptone, serum, and/or starch containing medias), defined growth media, or a selective media (e.g., nutrient selective for mannitol, cysteine, lactose, sucrose, salicin, xylose, lysine, or combinations thereof; selective based on carbon source, nitrogen source, energy source, and/or essential amino acids, lipids, vitamins, minerals, trace elements, or other nutrients; and/or selective antibiotic/antimicrobial containing media). Exemplary growth media that may be used in solid (e.g., with agarose) or liquid form include R2A, nutrient, chocolate blood, blood, mannitol salt, Vogel Johnson, Kligler iron, Simmons citrate, Columbia, cetrimide, xylose-lysine-deoxycholate, tryptic soy, Tinsdale, Phenylethyl alcohol, Mueller-Hinton, MacConkey, brain-heart infusion (BHI), and lysogeny broth media.

In preferred embodiments, the first growth medium is a liquid growth medium. In one particular example, the sample is a blood sample, and the growth media is selected as serum (e.g., human, bovine) and/or brain-heart infusion (BHI) broth, and may be contacted with the blood sample as a liquid in suspension with the blood sample. In preferred embodiments the growth media is formulated without substances that would hamper or restrict the growth of any bacteria found within the sample. For example, the growth media preferably omits antimicrobial enzymes (e.g., lysozyme, protease, etc.), antimicrobial peptides, and immune system components (e.g., leukocytes, complement system proteins, antibodies or other immunoglobulins, etc.).

For example, it has been discovered that L-form bacteria are often able to reside within a sample at a low-grade level without eliciting a full immune response and without progressing to classic form. The presence of immune system components or other growth hampering substances within such samples can prevent the bacteria from being manifest in classic form, even though the bacteria are present within the sample in L-form. Under such circumstances, the removal or dilution of growth hampering substances and/or the transfer of L-form bacteria to growth media without growth hampering substances can promote progression of the bacteria within the sample to classic form, and thereby provide faster culture and screening of L-form bacteria within the sample.

In an example where blood is used as a sample, the first set of incubation conditions promote the aging of the blood cells, allowing L-form bacteria present within the cells to progressively grow. For example, as white blood cells die and as red blood cells rupture, more L-form bacteria are able to escape their intracellular positions and move into the surrounding extracellular medium. In addition, the dilution of the sample within the first growth medium dilutes the concentration of antibodies and other humoral immune system components present within the blood sample, also enabling greater growth of the L-form bacteria.

In some embodiments, immune system components may be removed from the sample or from the inoculated first growth medium, or can be inactivated by adding an inactivating agent, such as a binding compound or complement inactivator, by adding one or more blocking antibodies, by washing, centrifuging, and/or filtering the sample to separate cells from other immune system molecules, or simply by diluting the sample sufficiently within the growth medium to render the components ineffective. In preferred embodiments, however, substances that would hamper PCR or other analysis techniques (such as ethylenediaminetetraacetate (EDTA)), or that would inhibit reversion to classic form (such as EDTA), are omitted.

After the sample is contacted with the first growth medium in step 120, the method proceeds to step 130 by incubating the inoculated first growth medium under a first set of incubation conditions. The collected sample is stored at a temperature about body temperature or at a temperature lower than about body temperature. For example, the collected sample may be stored at a temperature, constant or fluctuating, within a range or about 20 to about 40 degrees C., or within a range of about 25 to about 35 degrees C., or more preferably within a range of about 25 to about 30 degrees C., or about 27 degrees C. In preferred embodiments, the inoculated first growth media is stored at a temperature that is below body temperature. It has been surprisingly found that L-form bacteria within a sample grow at a greater rate at temperatures lower than body temperature. For example, in human blood samples, which are typically stored at body temperature (37 degrees Celsius), it has been found that storage at a lower temperature increases the growth of L-form bacteria within the sample and enables L-form bacteria which would otherwise remain present in non-detectable levels to grow to observable levels. Preferably, incubation also omits rocking or shaking of the growth medium in order to reduce the amount of contact between any L-form bacteria and any antibodies or other immune components within the sample.

The inoculated first growth medium is incubated for a time sufficient to provide growth of any L-form bacteria present within the sample (e.g., for a time sufficient to allow any L-form bacteria present within the sample to achieve a detectable population). In some embodiments, this monitoring period can be about 120 hours or even longer than 120 hours. In more preferred embodiments, this monitoring period can be less than about 120 hours. For example, in some embodiments, the monitoring period can be within a range of about 24 to about 96 hours, or within a range of about 36 to about 84 hours. In other embodiments, the monitoring period is within a range of about 48 to about 72 hours.

Step 140 of monitoring the first growth medium during the monitoring period for the presence of any L-form bacteria may be performed using an embodiment of the sample collection device herein, or may, in other embodiments, be carried out by transferring the sample or a portion of the stored sample to a microscope slide, well plate, or other such apparatus allowing the microscopic visualization of the sample or portion of the sample. In preferred embodiments, in order to avoid the disruption of potentially fragile L-form bacteria within the sample or portion of the sample collected for microscopic inspection, the visual monitoring is carried out without traditional staining (e.g., Gram staining) or chemical or heat fixing steps. For example, the visual monitoring may be carried out by direct microscopic observation of the sample or portion thereof by preparing a wet-mount, live slide for observation. Although microscopy using live slides is the preferred manner of monitoring for L-form growth, other suitable monitoring techniques include spectrophotometric methods (including colorimetry and measurement of optical density), staining, and measurements of turbidity, total cellular DNA and/or protein levels, electrical field impedance, bioluminescence, carbon dioxide, oxygen, ATP production or consumption, and the like.

Monitoring of the first growth medium may be carried out throughout the monitoring period. For example, monitoring may occur periodically according to a set schedule throughout the monitoring period, such as at set intervals (e.g., daily, every 12 hours, every 10, 8, or 6 hours, every 4, 3, or 2 hours, hourly, or even more frequently). In some circumstances, a sample may be monitored throughout a monitoring period, and may fail to exhibit any indication of bacterial infection. At this point, in some embodiments, the method is completed and a negative result is returned (e.g., the method either detected or failed to detect the presence of any infection in the sample).

Figure 2:
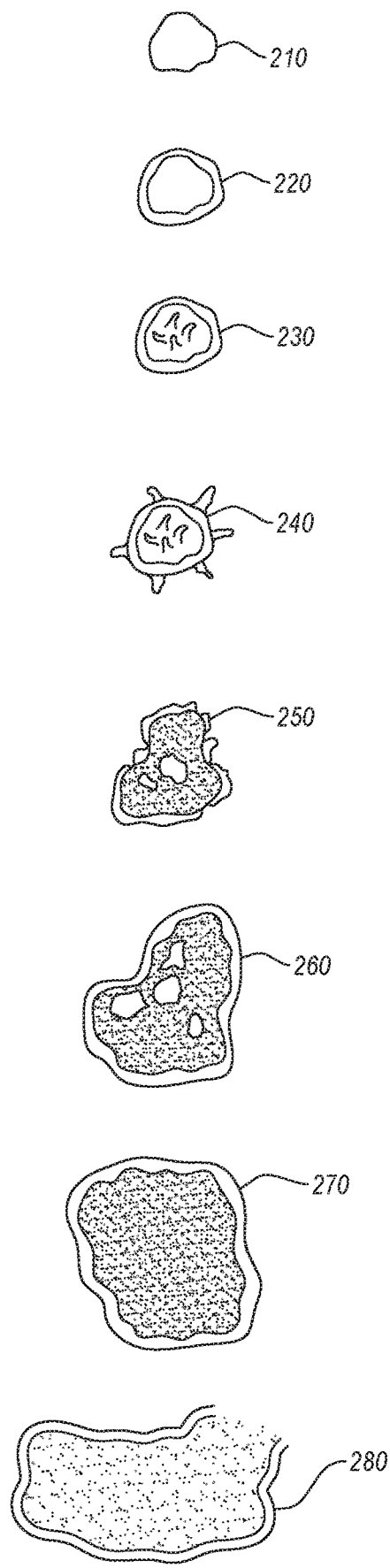
FIG. 2 illustrates the progression of an aging red blood cell infected with L-form bacteria.

Prior to transferring to a second growth medium, the inoculated first growth medium is preferably incubated until L-form bacteria within the medium have progressed to a state of sufficient growth. In an example where blood is a sample, FIG. 2 illustrates a typical progression of a red blood cell harboring L-form bacteria once placed under the first set of incubation conditions. A healthy red blood cell 210 that harbors L-form bacteria will begin to progress to a first state 220, where internal pressure is created by developing L-form bacteria within the cell. At a second state 230, L-form bacteria begin to transition from a non-microscopically observable form (e.g., under about 0.05 µm) to an observable form. At a third state 240, internal structures of the red blood cell begin to break down (e.g., through the action of lysozymes), freeing up additional nutrients for L-form growth and creating greater internal pressure within the cell. In some circumstances it has been observed that many cells stay at this state for long periods of time (e.g., several weeks or months). L-form bacteria appear to be present in such cells, but the L-form bacteria are not released from the cells at detectable levels. When these types of cells are present, embodiments utilizing a comminuting step may be particularly advantageous. In other circumstances, cells continue toward further states. At a fourth state 250, outward protrusions of the cell become visible through weak spots in the wall of the degrading red blood cell. At a fifth state 260 and a sixth state 270, the cell wall further breaks down and the cell continues to expand toward its limits. At a seventh state 280, the cell ruptures due to degradation and excessive internal bacterial growth, releasing L-form bacteria into the surrounding growth medium.

Preferably, the inoculated first growth medium is incubated until at least some (e.g., 10% or more, 25% or more, 50% or more, 75% or more, 90% or more) of the monitored cells of the sample have progressed to a state where they have ruptured to release intracellular L-form bacteria.

Some embodiments further include a step 150 of transferring at least a portion of the inoculated first growth medium to a second growth medium, and a step 160 of incubating the second growth medium under a second set of incubation conditions. In preferred embodiments, the second growth medium is a solid-phase growth medium (e.g., contained in a plate or slant). For example, solid-phase growth media may include one or more of the growth media described above (e.g., complex media, defined media, minimal or selective media) incorporated into a solid substrate. Suitable solid substrates include those formed with agarose, collagen, laminan, elastin, peptidoglycan, fibronectin, and the like.

The second set of incubation conditions includes a temperature within a range of about 20 to about 40 degrees C. Preferably, the second growth medium is incubated at approximately body temperature (about 30 to 40 degrees C. or about 37 degrees C.). The second growth medium is incubated at this temperature for a time period of about 24 to 96 hours, or about 36 to 84 hours, or about 48 to 72 hours, or about 60 hours. In some embodiments, the temperature is then adjusted to a range that is below body temperature (e.g., about 25 to 35 degrees C., or about 25 to 30 degrees C., or about 27 degrees C.) for a time period of about 4 to 30 days, or about 7 to 21 days, or about 14 days.

In some embodiments, the step 150 includes transfer to multiple types of solid-phase growth media in order to isolate multiple strains that may be present within the sample. For example, a set of agar plates may be prepared to receive the sample, with several of the agar plates containing different forms of media (such as any of those types discussed above with respect to the sample collection device, including selective growth media), and these may be further divided by placing one set under aerobic conditions after inoculation and another set under anaerobic conditions after inoculation (e.g., by placing in a standard anaerobic chamber maintained with carbon dioxide). During or after incubation, the method can include the step 170 of monitoring the second growth medium for bacterial growth (e.g., using one or more of the monitoring techniques described herein).

Although defined medias may be used as growth media in the methods described herein, it has been found that L-form bacteria are able to be efficiently cultured and detected using various complex medias such as BHI medias or those including serum (as the first and/or second growth medias). Beneficially, the methods described herein have enabled the screening of L-form bacteria without the need for generally more expensive defined medium formulations. Without being bound to any particular theory, it is thought that one or more process steps, such as the particular incubation conditions (e.g., time, temperature) and/or transfer steps (e.g., transferring bacteria in a manner that enables bacteria within a sample to maintain a hydrated state) utilized enables L-form bacteria to be cultured without the need for custom-made or defined medias.

Referring back to FIG. 1, some embodiments further include a step 180 of isolating bacteria grown on the second growth medium. As growth occurs on the second growth medium, some strains of L-form bacteria may transition to classic form and may grow classic form colonies on the second growth medium. Such bacteria may transferred to separate media (e.g., one or more complex, selective, or defined medias described herein) until a single strain is found on the media, and/or may be sampled and further analyzed according to well-known microbiological characterization techniques, including microscopic examination, staining (e.g., Gram, Malachite green/Safranin, and acid-fast stains), and selective growth testing. Other analytical techniques such as chromatography, gel separation, immunoassays, flow-through assays (e.g., plasmon resonance detection), fluorescent probe binding and measurement, automated cell/plate counting, microwell reading, and DNA hybridization and amplification methods (e.g., polymerase chain reaction, strand displacement amplification), may also be used to analyze bacteria cultured or isolated using the methods described herein.

Antimicrobial Production & Analysis

In some embodiments, bacteria that have been cultured and/or isolated using the second growth medium may be tested against one or more antimicrobial compounds (e.g., minimum inhibitory concentration tests). Some strains of bacteria may not be fully susceptible or fully resistant to a given concentration of a given antibiotic, but rather may revert back to L-form when exposed to the given concentration of the given antibiotic. Additionally, some strains or combinations of strains may form biofilms when exposed to a given concentration of a given antibiotic.

In some embodiments, analysis of antibiotic sensitivity can be carried out using a live slide technique. For example, a slide can be prepared by placing water, saline, or a combination of water, saline, and/or an antibiotic compound on a slide and contacting bacteria to the slide. Optionally, a layer of sterile petroleum jelly or other sealing compound may be placed on the slide prior to addition of the water, saline, and/or combination including an antibiotic compound. After the bacteria have been added to the slide, a slide cover can be placed over the slide (and sealed in place in those embodiments including a petroleum jelly or other sealing material).

In some embodiments, a cultured or isolated bacterial strain is used for the production of antibodies, vaccines, diagnostic reagents, and/or other useful compounds. In some embodiments, a method for detecting the presence of L-form bacteria within a sample and/or diagnosing a subject as having an L-form bacterial infection can include collecting a sample from a subject, and exposing the sample to a complete antibody, wherein interaction of one or more components of the sample with the complete antibody indicates the presence of L-form bacteria within the sample.

For example, a complete antibody can be harvested from serum (e.g., serum collected from a human or animal known or expected to have been exposed to an L-form bacteria and/or to have produced complete antibodies) by subjecting the serum to one or more purification processes. The one or more purification processes can include, for example, physiochemical fractionation such as size-exclusion chromatography, ion exchange chromatography, melon gel chromatography, other chromatography processes, zone electrophoresis, ammonium sulfate precipitation or other precipitation processes, and/or thiophilic adsorption or other solid-phase binding processes. The one or more purification processes can also include, for example, ligand affinity purification processes such as protein A, G, and/or L ligand binding. In some embodiments, a complete antibody (e.g., a complete antibody purified as described above) can be used to probe and/or diagnose the presence of an L-form bacteria and/or L-form related antigen through, for example, Western blotting, enzyme-linked immunosorbent assay (ELISA), and the like.

In some embodiments, one or more antibiotics and/or complete antibodies may be used to treat a subject having an L-form bacterial infection. For example, one or more antibiotics that have been screened as effective against an L-form bacteria (e.g., the specific L-form bacteria causing the infection) and/or one or more complete antibodies (e.g., complete antibodies capable of immunological interaction with the specific L-form bacteria causing the infection) can be administered to a patient in order to treat the L-form bacterial infection.

Sample Comminution

In some circumstances, it may be desirable to subject a sample to blending, vortexing, sonication, or other disruptive processes or combinations thereof in order to disassociate biofilms and/or aggregates, to rupture cells, or to otherwise disperse any bacteria and increase exposure to surrounding growth media prior to further screening. It has been surprisingly found that proper use of a comminution step in a screening process can increase yields, reduce culture times, and allow for faster detection and diagnoses of samples having L-form bacteria. Although the exemplary method may be used to prepare any of the forms of samples defined above, it may be particularly useful in preparing samples known to contain, or known to be likely to contain, biofilms and/or other aggregates potentially harboring L-form growth.

Figure 3:
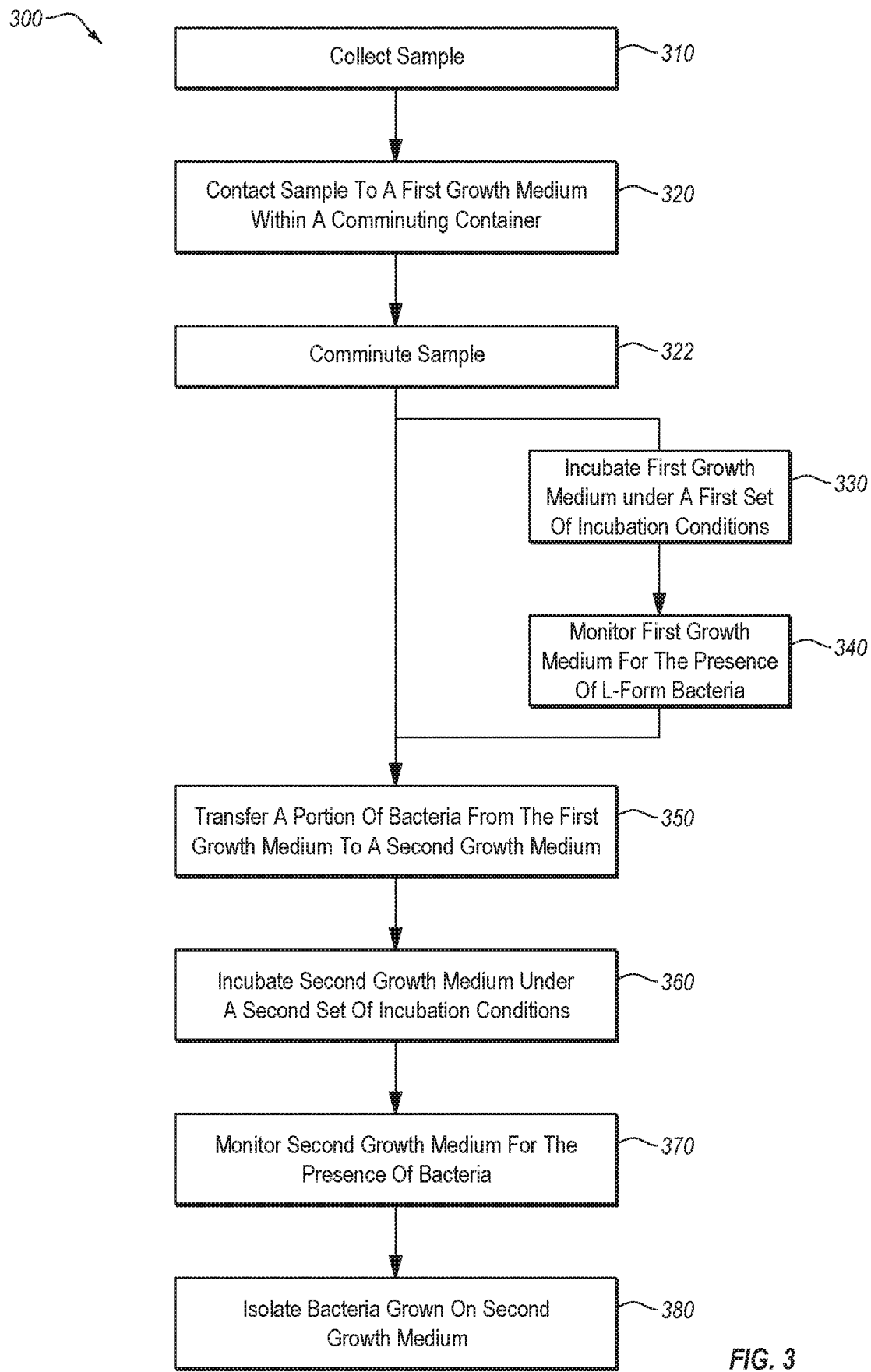
FIG. 3 illustrates a method for screening for L-form bacteria including comminution of the sample.

FIG. 3 illustrates another exemplary method 300 of screening for L-form bacteria that includes comminution of the sample. The embodiment shown in FIG. 3 has steps and elements similar to the embodiment shown in FIG. 1, and like numbers represent like elements. As illustrated, the method includes a step 310 of collecting a sample, and a step 320 of contacting the sample to a first growth medium. In some embodiments, the first growth medium is contained within a comminution container. The comminution container is typically formed as an elongate tube with a rounded bottom portion, or with a tapering (e.g., conical frustrum) shaped bottom portion.

The comminution container includes a comminuting media configured to contact the sample and disaggregate biofilms, cell clumps, and other aggregates within the sample. The comminuting media is preferably formed from crushed or shattered glass. Other embodiments may include comminuting media formed from beads, shards, particles, fragments, filaments, or other structures configured to contact the sample and disassociate particles within the sample, and may be formed out of metal, plastic, ceramic, or other materials or combinations of materials.

The exemplary method includes a step 322 of comminuting the sample. In some embodiments, the sample and first growth medium are vortexed (e.g., by placing the comminuting container in a vortex apparatus) to displace the comminuting media within the liquid and to enable contact between the comminuting media and the aggregated portions of the sample. In other embodiments, the sample may be comminuted using magnetic stirring (e.g., one or more magnetic stir bars included in the comminuting media), or by shaking, vibrating, or otherwise displacing the comminuting media.

In some embodiments, after comminuting, the method includes a step 330 of incubating the inoculated first growth medium under a first set of incubation conditions and a step 340 of monitoring the inoculated first growth medium for the presence of L-form bacteria. Alternatively, after comminuting, the method can proceed to a step 350 of transferring a portion of the first growth medium to a second growth medium (preferably a solid growth medium) without prior incubation of the sample. Such embodiments can beneficially reduce the culture time required before a diagnosis can be made and/or before bacteria can be isolated and analyzed. For example, the progression of infected red blood cells shown in FIG. 2 can be effectively bypassed or made to progress more rapidly. In some embodiments, the method then proceeds through a step 360 of incubating the second growth medium under a second set of incubation conditions, a step 370 of monitoring the second growth medium for the presence of bacteria, and optionally a step 380 of isolating bacteria grown on the second growth medium, as described above.

Inoculant Transfer

Figure 4:
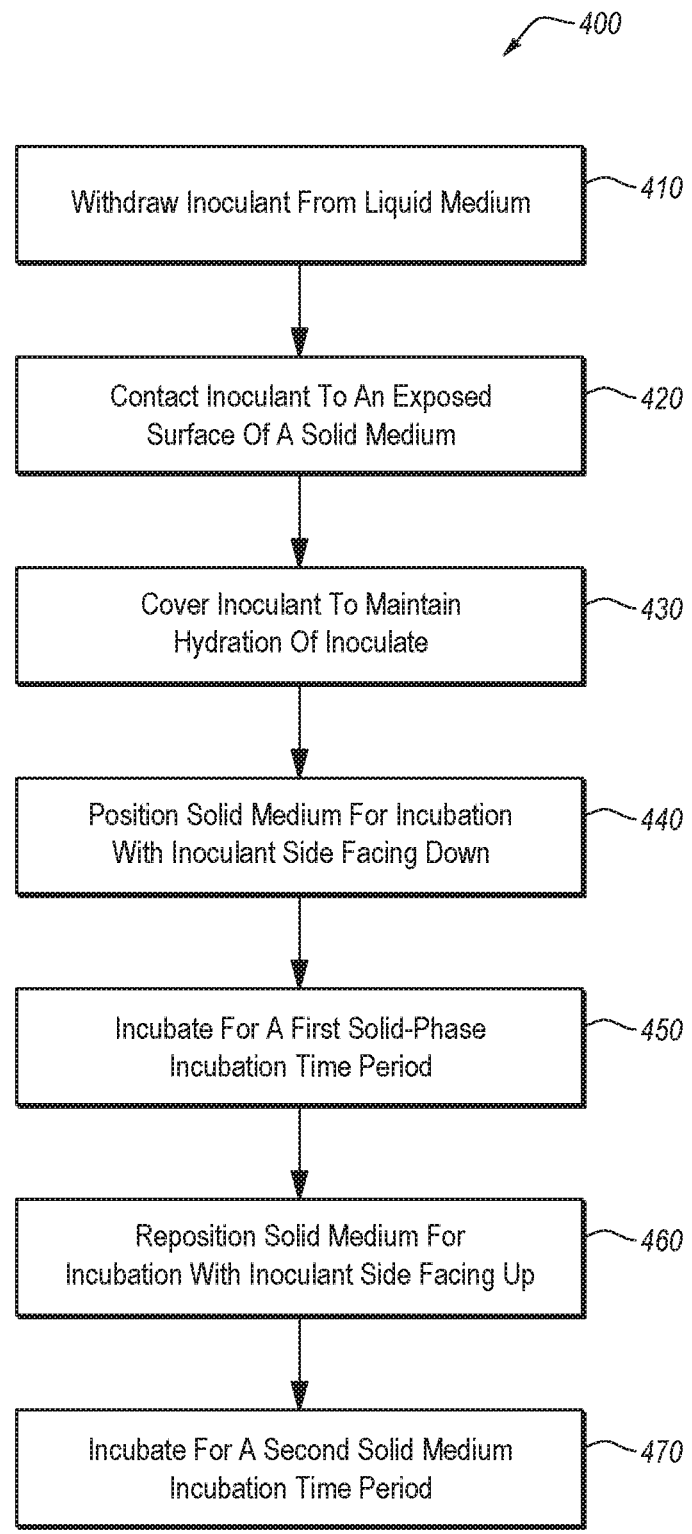
FIG. 4 illustrates an exemplary method for transferring an L-form inoculant from a liquid growth medium to a solid growth medium.

FIG. 4 illustrates an exemplary method 400 for transferring an inoculant from a first, liquid growth medium to a second, solid growth medium and incubating the solid growth medium (e.g., as part of the steps 150 and 160 in the embodiment of FIG. 1 or the steps 350 and 360 in the embodiment of FIG. 3). As shown, the method includes a step 410 of withdrawing an inoculant from the liquid medium, and a step 420 of contacting the inoculant to a surface of a solid medium.

After contacting the inoculant to the solid medium, the method includes a step 430 wherein the inoculant is immediately (e.g., within seconds or within about 1 or 2 minutes) covered by an insert in order to maintain a hydrated state of the inoculant. It has been found that positioning the insert over the inoculant beneficially enables L-form bacteria within the inoculant to interface with the solid substrate to begin colonization of the solid medium. It is theorized that L-form bacteria are often in a hydraulically fragile state at this point in culturing (e.g., due to reduced or absent cell wall structures), and that excessive drying and/or too rapid concentrating of solutes within the inoculant containing the L-form bacteria can inhibit further culturing of the L-form bacteria, increasing the probability of false-negative diagnoses.

In some embodiments, the insert is a glass panel, glass slide, or other material configured to sit upon the solid media and preferably, to maintain position relative to the solid media (e.g., through adhesive forces between the inner surface of the insert contacting the inoculant and the inoculant). Other embodiments may include inserts made from rigid or film plastics, ceramics, or other materials. Preferably, the insert is positioned to eliminate air pockets within the inoculant between the surface of the solid media and the inner surface of the insert. In some embodiments, an additional amount of inoculant may be contacted to other portions of the surface of the solid media not covered by the insert, if any.

In some embodiments, the method further includes a step 440 of positioning the solid medium for incubation with the inoculant side facing down. For example, where an agarose plate is used to contain the solid media, the plate is positioned "upside down" so that the surface to which the inoculant and insert were applied faces down.

In some embodiments, the method further includes a step 450 of incubating the solid medium for a first solid-phase incubation time period of about 4 to 24 hours, or about 6 to 18 hours, or about 12 hours. The incubation may be carried out under the temperature conditions described in relation to step 160 of FIG. 1. Preferably, the incubation is also carried out in an atmosphere having a relative humidity that is sufficient to prevent overly rapid drying of the inoculant.

As explained above, it has been discovered that greater culturing efficiency and greater diagnostic accuracy are made possible by maintaining a hydrated state of the inoculants and growth media as the disclosed methods are performed. For example, during the first solid-phase incubation time period, the relative humidity may be maintained within a range of about 40 to 100%, or about 50 to 90%, or about 60 to 80%. In some embodiments, the method further includes a step 460 of repositioning eth solid medium with the inoculant side up. It has been discovered that, at this point in the progression of L-form cultures, the L-form bacteria have typically progressed enough and/or the insert has sufficiently interfaced with the solid medium, such that the benefits of repositioning the solid medium to allow evaporation of water that has built up in the inverted position outweigh the detrimental effects, if any, of repositioning.

In some embodiments, the method further includes a step 470 of incubating the solid medium for a second solid-phase incubation period. The second solid-phase incubation time period is preferably performed in an atmosphere having similar relative humidity levels of the first solid-phase incubation time period, and for a time period ranging from about 12 to 84 hours, or about 24 to 72 hours, or about 36 to 60 hours, or about 48 hours. In some embodiments, one or more cultures are further incubated at a temperature in a range that is below body temperature (e.g., about 25 to 35 degrees C., or about 25 to 30 degrees C., or about 27 degrees C.) for a time period of about 4 to 30 days, or about 7 to 21 days, or about 14 days.

Sample Collection Device

Figure 5A:
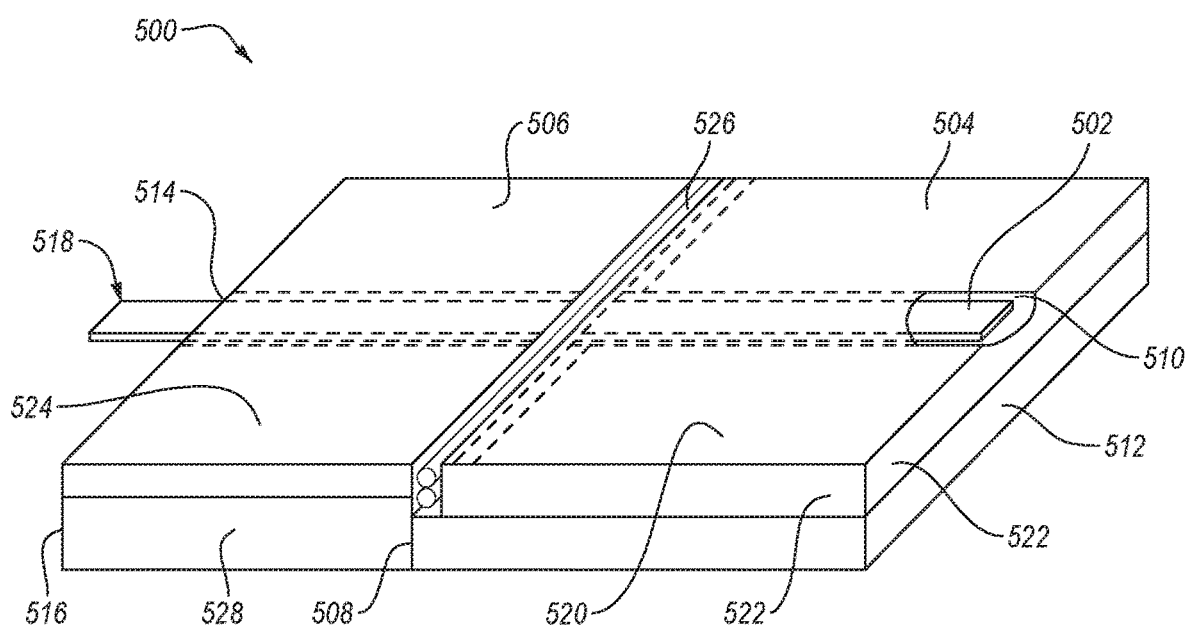
FIGS. 5A to 5E illustrate an exemplary sample collection device.
Figure 5B:
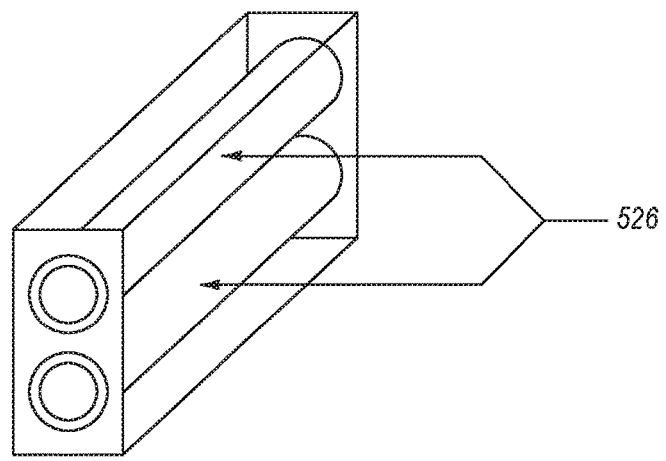

FIGS. 5A and 5B illustrate an embodiment of a sample collection device 500 including a sample carrier 502, a first section 504, and a second section 506. The first section 504 and the second section 506 may be integrally formed as one piece with one or more partitions 508 separating the first and second sections. In other embodiments, the first and second sections 504 and 506 may be formed separately and joined together through an attachment means, such as an adhesive and/or a mechanical linkage.

In certain embodiments, the first section 504 and second section 506 are selectably detachable, such that the first section 504 and second section 506 may be selectably separated from each other. For example, the first section 504 and the second section 506 may be coupled by a section of weakened structural integrity, allowing the first section and the second section to be separated by breaking or splitting the section of weakened structural integrity. In other embodiments, the first section 504 and second section 506 may be selectably detachable through other means, such as by unfastening one or more mechanical linkages (e.g., clasps, clamps, locks, or other fasteners).

The first section 504 and second section 506 are configured such that at least a portion of the sample carrier 502 can be received by each of the first section 504 and second section 506. As shown in FIG. 5A, the sample carrier 502 and first and second sections 504, 506 are configured in size and shape so as to allow the sample carrier 502 to pass through an input port 510 at a first side 512 and extend through to an exit port 514 at a second side 516. In other embodiments, the sample carrier 502 may extend only partially through the sample collection device 500 and/or any input ports 510 and exit ports 514 may be disposed at other locations on the sample collection device 500, such as on the top surface.

As described in more detail below, the sample carrier 502 is configured to receive and associate with a sample. In some embodiments, the sample carrier 502 may be formed as a wick capable of absorbing and incorporating a sample contacted with a portion of the wick. In other embodiments, the sample carrier 502 may be formed as a sample collection surface or sample receiving area, wherein a sample may be placed into or upon the sample collection surface or receiving area before being channeled or otherwise directed into the device. In such embodiments, the sample carrier 502 may be formed from a variety of materials or combinations of materials, including glass, metals, plastics, ceramics, fibers, and other materials. In other embodiments, the sample carrier is omitted, and a sample may be directly delivered to the first section and/or second section of the sample collection device. In embodiments wherein the sample carrier is a wick, the wick may be formed, for example, from a synthetic or natural fibers, such as cotton, wool, hemp, flax, sisal, jute, nylon, acrylic, polyester, and the like. The sample carrier 502 may be formed as a cord, rope, string, or similar shape (e.g., a shape having a generally circular cross-section). In other embodiments, the sample carrier 502 may be formed as strap or strip, having a generally flat, rectangular cross-section. In other embodiments, the sample carrier 502 may have a different construction, such as other polygonal cross-sections or a cross-section that is irregular and/or non-uniform.

In the embodiment shown in FIG. 5A, the sample carrier 102 extends into a sample input port 510 near a first side 512 of the sample collection device 500 to and beyond an exit port 514 near a second side 516 of the sample collection device 500. In this configuration, the sample carrier 502 may be pulled through the device (e.g., by gripping the extending portion disposed beyond the device as a pulling end 518 and pulling the pulling end 518 further beyond the exit port 514) such that at least a portion of the sample carrier 502 moves through the first section 504 of the sample collection device 500 and into the second section 506 of the sample collection device 500.

Certain embodiments may include one sample carrier 502. In such embodiments, the sample carrier 502 is preferably disposed across both the first section 504 and the second section 506, or is otherwise configured to be moveable from one portion to the other portion in order to deliver a portion of the received sample to both the first and second sections. In other embodiments, the sample collection device 500 may include more than one sample carrier 502. For example, in some embodiments, a first sample carrier may be associated with the first section and configured to deliver or contact a sample to the first section, and a second sample carrier may be associated with the second section and configured to deliver or contact a sample to the second section.

In the embodiment illustrated in FIG. 5A, the first section 504 is configured to receive a portion of the sample from the sample carrier 502 into a first growth area 520 in order to culture any L-form bacteria present within the sample in the first growth area 520. For example, the first section 504 may include a sample receiving surface 522 suitable for receiving at least a portion of the sample and for allowing growth of any L-form bacteria present within the sample. In some embodiments, the sample receiving surface 522 of the first section 504 includes a sealing material (not shown) or other means of preventing dry-out of the sample. For example, in some embodiments the sample receiving surface 522 may be coated in whole or in part with a petroleum jelly or other sealing and/or waterproofing material, such as wax, caulk, paraffin, putty, or the like. When the sample is sealed within the first growth area 520 (e.g., using an insert as described in detail below), the sealing material aids in preventing dry-out of the received sample.

In certain embodiments, the first growth area 520 includes a solid-phase growth medium or surface (e.g., an agar surface) incorporating various types and/or combinations of growth media, such as those described above. In the illustrated embodiment, the second section 506 is configured to receive a portion of the sample from the sample carrier 502 and to culture any L-form bacteria present within the sample in a second growth area 524. In the illustrated embodiment, the second growth area 524 may include a suspension chamber 528 suitable for holding a liquid medium and supporting bacterial colonization and growth in suspended form. The suspension chamber 528 may incorporate any of the growth media described above, in liquid form.

The illustrated embodiment also includes a sample extractor 526. In the illustrated embodiment, for example, the sample extractor 526 is disposed between the first section 504 and the second section 506, and is configured to cooperate with the sample carrier 502 in order to extract or remove at least a portion of the sample associated with and/or joined to the sample carrier 502. In this embodiment, and as additionally shown in FIG. 5B, the sample extractor 526 includes two opposing compression rollers with longitudinal axes generally aligned and in parallel with each other, the longitudinal axes of the compression rollers disposed at an angle transverse to a direction of longitudinal extension of the sample carrier 502.

The illustrated sample extractor 526 is configured to receive a portion of the sample carrier 502 and to compress against the portion of the sample carrier 502 in contact with the sample extractor 526, thereby forcing at least a portion of the sample associated with the sample carrier 502 out of and/or away from the sample carrier 502 and into the first growth area 520. In the illustrated embodiment, for example, the sample carrier 502 is inserted between the opposing compression rollers. As the sample carrier 502 is moved in a direction transverse to the longitudinal axes of the opposing compression rollers, different portions of the sample carrier 502 are successively placed between the opposing compression rollers and are compressed by the compression rollers, thereby extracting at least a portion of any sample associated with that portion of the sample carrier 502.

In other embodiments, two or more sample extractors may be included, and/or the sample extractor(s) may be disposed at other locations of the sample collection device. For example, a first sample extractor may be disposed closer to the first side of the sample collection device, and a second sample extractor may be disposed farther from the first side of the sample collection device. In such an embodiment, the first and second sample extractors may be configured to deliver different (e.g., progressively higher) levels of extraction force in order to progressively extract additional amounts of sample from the sample carrier. The first and second sample extractors (and additional extractors, if included) may direct extracted sample material to a common growth area or to separate growth areas.

In other embodiments, the sample extractor(s) may be formed as other sample extraction means. For example, a sample extractor may include a single roller, or may include a plurality of multiple rollers configured to press against a sample carrier as it passes through roller configuration (e.g., a belt-press configuration). In other embodiments, a sample extractor may be configured as one or more posts, bars, or surfaces contacted with the sample carrier as the sample carrier passes the sample extractor. In other embodiments, a sample extractor may be configured as a channel or passage of reduced cross-sectional area and/or a tortuous path forcing the compression of any portions of the sample carrier passed therethrough and/or dislodging portions of the sample adhered to the sample carrier surface. In other embodiments, a sample extractor may be configured as a manual or automatic press mechanism.

Some embodiments of a sample collection device include locking seals configured to seal and aseptically contain the collected sample and other interior elements (e.g., growth media, remaining portion(s) of sample carrier) within the sample collection device after a sample has been collected. In preferred embodiments, locking seals are disposed at any opening of the sample collection device. Additionally, one or more locking seals may be positioned between the first section 504 and the second section 506 in order to seal and separate the respective sections.

In preferred embodiments, locking seals are formed, at least in part, of a material capable of sealing against adjacent portions of the sample collection device in order to form an aseptic seal (e.g., water and/or airtight seal). For example, a locking seal may include a rubber surface disposed on one or more sides of the locking seal configured so as to press against adjacent portions of the sample collection device when moved toward or into a closed/locked position. In some embodiments, one or more locking seals may include a cutting element configured to cut the sample carrier 502 as the locking seal is moved from an open position toward a closed, sealed position. For example, a locking seal may include a cutting element formed at an end section of the locking seal such that as the locking seal is moved from an open position toward a closed position (e.g., as the locking seal is slid sideways, or moved downward or upward), the cutting element is passed across a plane extending from an opening of the sample collection device (e.g., an exit port 514).

Figure 5C:
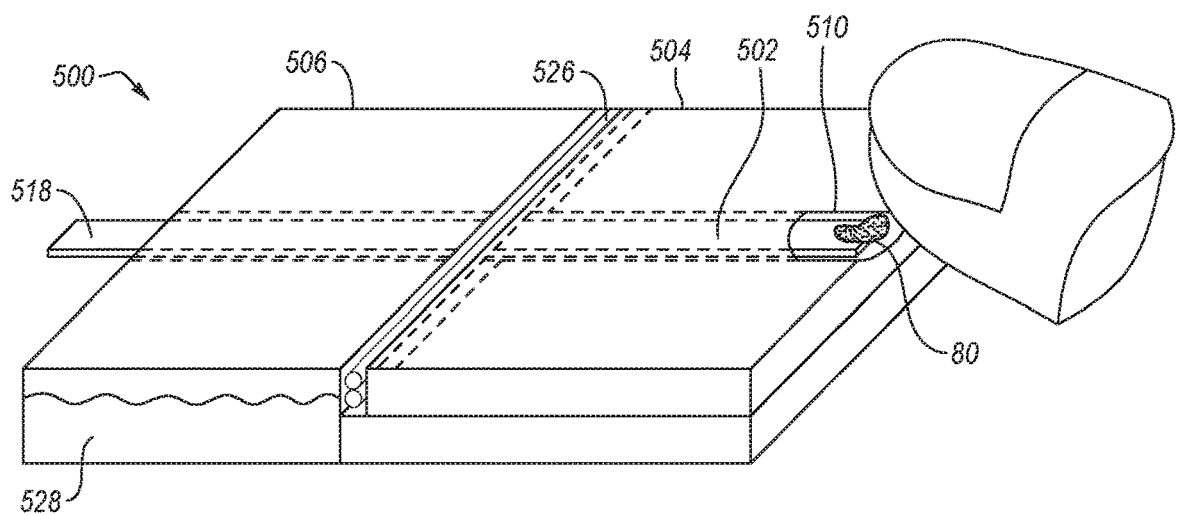
Figure 5D:
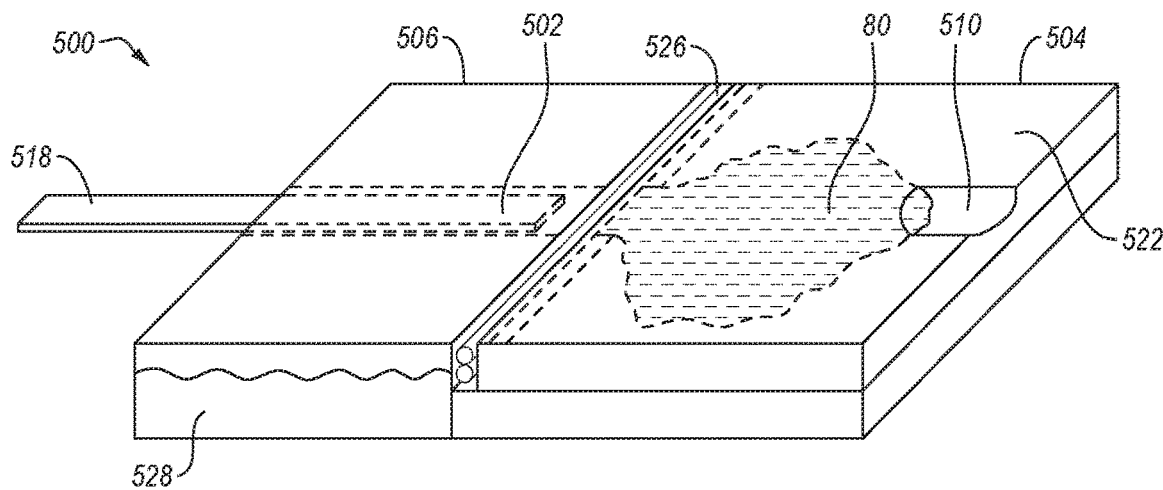
Figure 5E:
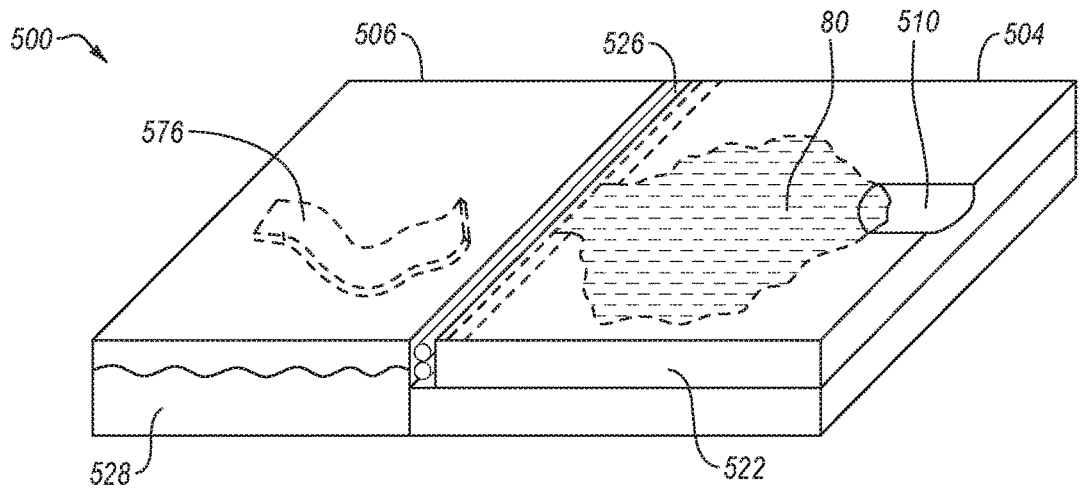

FIGS. 5C to 5E illustrate one embodiment of a process of providing a sample to a sample collection device 500. As shown in FIG. 5C, a sample 80 is contacted with the sample carrier 502 at the input port 510. In the illustrated embodiment, the sample 80 is a blood sample obtained by finger prick method. After the sample 80 has associated with the sample carrier 502, the sample carrier 502 is partially moved through the sample collection device 500 by grasping the pulling end 518 and moving the pulling end 518 further from the sample collection device 500. As this is done, portions of the sample carrier 502 originally positioned within the first section 504 of the device are moved through the sample extractor 526, and a portion of the collected sample 80 is extracted from the sample carrier 502 and received by the sample receiving surface 522 of the first section 504.

In the illustrated embodiment, the portion of the sample carrier 502 remaining in the second section 506 after moving the sample carrier 502 partially through the sample collection device 500 is cut so as to leave a remaining portion 576 in the second section 506. In the illustrated embodiment, the second section 506 includes a suspension chamber 528 containing a liquid growth medium. The remaining portion 576 of the sample carrier 502 contains residual portions of sample 80 that serve to inoculate the suspension chamber 528 so that any bacteria within the sample 80 can be cultured in suspended form within the suspension chamber 528. As discussed above, after the first and second sections 504 and 506 have received a portion of the sample 80, locking seals (not shown) may be used to aseptically seal the sample within the sample collection device 500 and to aseptically seal the first section 504 from the second section 506.

Figure 6A:
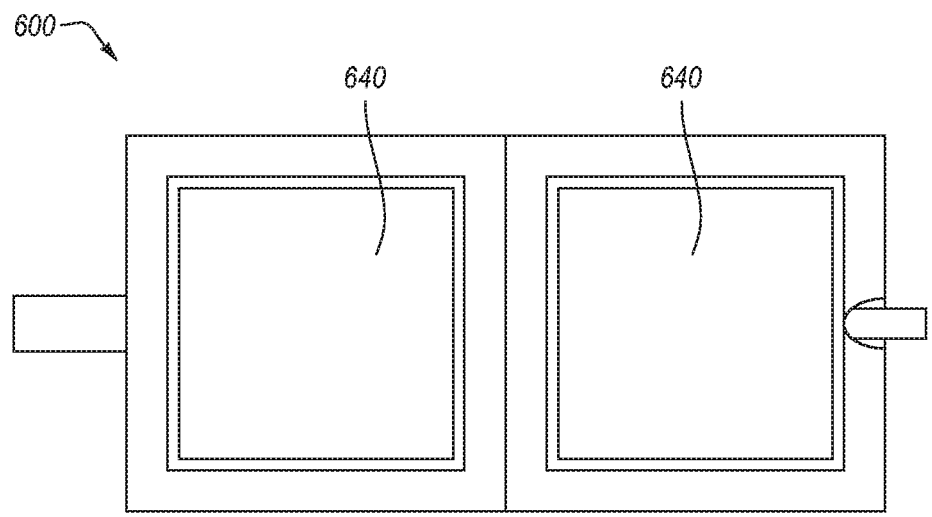
FIGS. 6A and 6B illustrate a viewing window of the sample collection device.
Figure 6B:
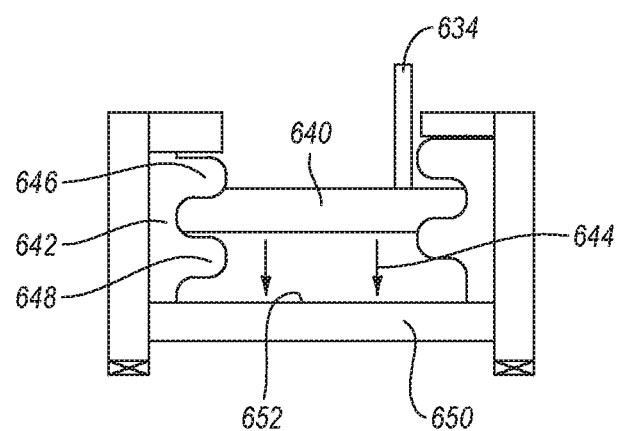

Some embodiments, as illustrated by the sample collection device 600 in FIGS. 6A and 6B, include one or more viewing covers 640. In the illustrated embodiment, the viewing covers 640 are configured to be moved from an open position toward and into a closed configuration. As shown in cross-section in FIG. 6B, a viewing cover 640 may be positioned in an open configuration by a pair of opposing supports in the form of support tabs 642 and 644 configured to support or otherwise hold the viewing cover 640 in an open position. The support tabs 642 and 644 may be configured in size and shape to be adjacent to the perimeter of the viewing cover 640 or portions thereof, as illustrated. In other embodiments, the supports may extend more or less to cover more or less of the area of the viewing cover 640.

As shown, a viewing cover 640 may be positioned in an open configuration to provide an open space 650 between the viewing cover 640 and an interior floor 652. The open space 650 is configured in size and shape to allow insertion and passage of the sample carrier (not shown) into and through the open space 650. After the sample carrier has been removed from the open space 650, either by passing through it or by dropping below it, the viewing cover 640 may then be moved from the open configuration toward and into a closed configuration. For example, the viewing cover 640 may be pressed or otherwise forced down against support tabs 642 and 644 such that the support tabs 642 and 644 flex to accommodate passage of the viewing cover 640. The support tabs 642 and 644 then flex back toward their original configurations, now functioning to hold and seal the viewing cover 640 in the closed or sealed position.

In preferred embodiments, the support tabs 642 and 644 are formed of a resiliently flexible material capable of supporting the viewing cover in an open or closed configuration while sufficiently flexing upon the application of a force (e.g., pushing or pulling) in order to allow passage of the viewing cover and transition from an open position toward a closed position and vice versa. Preferably, the support tabs are configured to form an aseptic seal (e.g., they are formed of rubber or similar material) around the viewing cover when positioned in closed configuration. The illustrated embodiment also includes a handle 654. The handle 654 extends from the viewing cover 640 and provides a means for gripping or otherwise holding the viewing cover 640 for easier movement between open and closed configurations.

In other embodiments, one or more viewing covers may be positioned in other locations, and/or may be configured to move from an open/closed position through other movement means. For example, some embodiments may include a static viewing window. In such an embodiment, for example, the viewing window may be positioned at a location suitable to allow sample viewing, while the sample carrier pathway and/or any other potentially interfering components are positioned at separate locations. In other embodiments, one or more viewing covers may be slid into grooves or channels in order to be received into a closed configuration. In other embodiments, one or more viewing covers may be coupled to a hinge or hinge-like mechanism allowing the viewing cover to be moved between an open configuration and a closed configuration by rotating the viewing cover upon the hinge(s).

Some embodiments include one or more fluid ports configured to allow injection or withdrawal of fluid into or from a suspension chamber (e.g., injection of growth media and/or withdrawal of sample and/or suspended culture). In some embodiments, a viewing cover includes a viewing chamber and an opening providing fluid communication between the viewing chamber and the bulk of the liquid growth medium adjacent to the viewing chamber. For example, the opening can enable fluid communication between fluid within the suspension chamber and the narrower viewing chamber. In this manner, suspension fluid may enter the viewing chamber, and the viewing chamber can provide a viewing plane for easier viewing and monitoring of the sample for bacterial growth.

Some embodiments may omit a first or second section. For example, some embodiments may include a sample carrier, an extractor, and a single growth area. Other embodiments may include more than two portions and/or growth areas. For example, several portions (e.g., three, four, or more) may be connected in series, and a single sample carrier may pass through the entire series. Alternatively, more than one sample carrier may be utilized in the series. Additionally, or alternatively, other portions may be arranged in parallel, with additional sample carriers configured to pass in the same direction or in alternating or opposing directions.

EXAMPLES

Example 1

Clinical samples were collected from 430 different individuals. The majority of the 430 samples were blood samples, with smaller numbers of synovial fluid samples and lymphatic fluid samples. A sample was taken from each subject and about 0.5 ml or less of the sample (about 2 drops) were added to a tube containing 10-15 ml of bovine serum and a tube containing 10-15 ml of BHI broth. The inoculated tubes were incubated at 27 degrees C. Development of L-form culture was monitored by preparing wet mount live slides daily. Samples were monitored for a period of up to 30 days. Samples that showed indications of L-form bacterial growth were typically incubated for at least 48 hours, and typically began to show signs of developing cell wall structures within 48-72 hours. L-form bacteria were not observed to progress to a complete classic form while within the plasma or broth.

For samples in which L-form bacterial growth was detected, the plasma and/or broth was used to inoculate a variety of agarose plates (mannitol salt, BHI, tryptic soy, tryptic soy w/5% sheep's blood, chocolate blood, Vogel Johnson, Simmons citrate, Columbia, brewer's yeast, nutrient, MacConkey, starch, and Kligler Iron agars). The inoculant was immediately covered with a sterile cover slide to prevent dehydration of L-form bacteria. Extra inoculant was streaked onto remaining portions of the agarose surface. A set of plates were then incubated at 37 degrees C. in an aerobic incubation unit, and a set were incubated at 37 degrees in an anaerobic chamber. Sterile water was supplied in order to maintain a humid environment within the incubation areas. The plates were placed agarose-side down for 12 hours, and then were flipped to agarose-side up and incubated for a further 48 hours. Plates were then removed and sealed in a plastic bag in order to retain moisture and were further incubated at 27 degrees for 14 days. At 14 days, plates were inspected for growth. Each colony was transferred to a set of nutrient agar and blood agar (trypticase soy agar with 5% sheep blood) plates.

Each isolated colony was tested using a BioLog GEN III MicroPlate 96 well plate. Results were compared to the BioLog catalog and species were listed in order of decreasing match percentage. A read was considered positive if the highest listing was greater than 50%, the first three species were of the same genus, and there was greater than 20% separation between listing 1 and 2.

The L-form growth protocols have resulted in the culture and isolation of over 1100 different bacteria. 251 different species were identified and 43 unknown bacteria were found. 11 of the isolated species were sent to an FDA certified lab for secondary analysis. Of the 11, 9 were identified as *Bacillus* species, one was a 99.5% match to a known *Bacillus*, and 1 was an unknown species.

Example 2

A comparative study was conducted to compare a standard culturing process to the process of Example 1. Each sample was divided into two portions. The first portion was used to directly inoculate two nutrient agars, which were then incubated and monitored for growth. The second portion was used as inoculant in the L-form growth protocol of Example 1. Results of the comparative study are shown in Table 1 (samples which showed no growth in either protocol are omitted).

TABLE 1

| Sample Type | Bacteria cultured via direct inoculation | Bacteria cultured via process of Example 1 |
|---|---|---|
| Blood | No growth | Acintobacter genomospecies 15tu |
| | | *Bacillus pumilus/safensis* |
| | | *Bordetella parapertussis* |
| | | *Simplicispira metamorpha* |
| | | *Micrococcus luteus* A |
| | | *Bacillus salentarsenatis/jeotigaii* |
| | | *Moraxella canis* |
| | | Unknown Rod |
| Blood | *Bacillus pumilus/safensis* | *Bacillus pumilus/safensis* |
| | *Staph. capitis* ss *urealyticus* | *Bacillus pumilus/safensis* |
| | | *Bacillus pumilus/safensis* |
| | | *Bacillus thuringiensis/cereus* |
| | | *Bacilus Vallismortis/subtilis* |
| Blood | No growth | *Bacillus plakortidis* |
| | | *Brachybacterium sacelii* (26C) |
| | | Unknown Bacteria |
| Blood | No growth | *Bacillus pumilus/safensis* |
| Blood | No growth | *Bacillus pumilus/safensis* |
| Blood | No growth | *Bacillus lichenformis* |
| | | *Bacillus lichenformis* |
| | | *Staphylococcus intermedius* |
| Blood | No growth | *Bacillus pumilus/safensis* |
| Blood | No growth | *Bacillus pumilus/safensis* |
| | | *Micrococcus luteus* B |
| | | *Corynebacterium terpenotabidum* |
| Blood | No growth | *Bacillus pumilus/safensis* |
| Blood | No growth | Unknown rod |
| Saliva | *Bacillus pumilus/safensis* | *Bacillus pumilus/safensis* |
| | | *Staphylococcus chromogenes* |
| | | *Staphylococcus warneri* |
| | | *Bacillus cereus/thuringiensis* |
| Synovial fluid | No growth | *Bacillus pumilus/safensis* |
| | | *Microccocus yunnanensis* |
| | | *Micrococcus luteus* A |
| Synovial fluid | No growth | *Bacillus pumilus/safensis* |
| | | Unknown |
| Synovial fluid | No growth | *Bacillus pumilus/safensis* |
| | | *Corynebacterium mycetoides* |
| | | *Sanguibacter keddieii* |
| | | *Bacillus megatarium* |
| | | *Micrococcus lylae* B |
| | | Unknown |
| Synovial fluid | No growth | *Bacillus pumilus/safensis* |
| | | *Acintobacter junii* |
| | | *Acintobacter lwoffii* |
| | | *Psycrobacter immobilis* |
| Synovial fluid | No growth | *Bacillus atrophaeus/subtillis* |
| | | *Bacillus lichenformis* |
| | | *Kytococcus aerolatus* |
| | | *Microccus luteus* E |
| | | *Microccocus yunnanensis* |
| | | *Staphylococcus epidermidis* |
| | | *Staphylococcus hominis* ss *homm* |
| | | *Micrococcus luteus* A |
| | | *Kocuria rhizophila* |
| Synovial fluid | No growth | *Bacillus pumilus/safensis* |
| | | *Micrococcus luteus* E |
| | | *Bacillus humi* |
| | | *Staphylococcus cohnii* ss *cohnii* |
| Synovial fluid | No growth | *Bacillus pumilus/safensis* |
| | | *Kytococcus aerolatus* |
| | | *Macrococcus equipercicus* |
| | | *Staphylococcus auricularis* |
| | | *Staphylococcus epidermidis* |
| | | *Staphylococcus capitis* ss *capitis* |
| | | *Staphylococcus aureus* ss *aureus* |
| | | *Micrococcus lylae* B |
| | | *Rhodococcus erythropolis* |
| | | *Cornebacterium freneyi* |
| Synovial fluid | No growth | *Bacillus pumilus/safensis* |
| | | *Bacillus pumilus/safensis* |
| | | *Kytococcus aerolatus* |
| | | *Kytococcus sedentarius* |
| | | *Microccocus yunnanensis* |

TABLE 1-continued

| Sample Type | Bacteria cultured via direct inoculation | Bacteria cultured via process of Example 1 |
|---|---|---|
| Baker cyst fluid | No growth | *Cornebacterium cystitidis*<br>*Cornebacterium auris*<br>*Staphylococcus capitis* ss *capitis*<br>Unknown fungus<br>*Bacillus pumilus/safensis*<br>*Bacillus sonorensis*<br>*Brevibacterium otitdis*<br>*Micrococcus luteus* E |

As shown, growth and culture of L-form bacteria to identifiable classic form was achieved using the process of L-form growth protocol of Example 1, even for many samples which gave no results and no growth under a standard direct inoculation technique. The results show that use of the L-form growth protocol can significantly reduce the occurrence of false-negative results in culturing and diagnostic testing of clinical samples.

The invention claimed is:

1. A method for culturing of L-form bacteria within a sample, the method comprising:
   (i) contacting a biological sample that has been treated to remove immune cell components to a first growth medium, wherein the first growth medium is a liquid, and wherein the first growth medium is a complex growth medium consisting of R2A media, chocolate blood, blood, Vogel Johnson media, Kligler's iron media, Columbia media, tryptic soy, Tinsdale media, Mueller-Hinton media, MacConkey media, brain-heart infusion (BHI) media, or lysogeny broth media;
   (ii) incubating the first growth medium at a temperature above 20° C. and below 37° C., under conditions omitting rocking or shaking, to form an inoculant;
   (iii) transferring a portion of the inoculant to a second growth medium, wherein the second growth medium is incorporated into a solid substrate;
   (iv) immediately covering the inoculant on the solid substrate with an insert;
   (v) incubating the solid substrate for less than thirty days under conditions that maintain a hydrated state of the inoculant on the sold substrate; and,
   (vi) monitoring the solid substrate for the presence of bacterial colonies.

2. The method of claim 1, wherein the biological sample is a blood sample, lymph fluid sample, mucous sample, cerebrospinal fluid sample, synovial fluid sample, or urine sample.

3. The method of claim 1, wherein the treatment to remove immune cell components comprises filtration of the sample.

4. The method of claim 1, wherein the method further comprises a step of monitoring the inoculant to detect the presence of L-form bacteria prior to transferring the portion of the inoculant to the second growth medium.

5. The method of claim 4, wherein the monitoring comprises visual monitoring by microscopy.

6. The method of claim 1, wherein the inoculant on the solid substrate is covered with an insert within seconds of the transfer.

7. The method of claim 6, wherein the insert is a glass slide or a glass panel.

8. The method of claim 1, wherein the second growth medium is selected from a complex growth medium, a defined growth medium, and a selective growth medium.

9. The method of claim 1, wherein the solid substrate is incubated with the inoculant side facing down.

10. The method of claim 1, wherein the solid substrate is incubated at a temperature between 30° C. and 40° C.

11. The method of claim 1, wherein the solid substrate is incubated at a relative humidity of about 40% to 100%.

12. The method of claim 1, further comprising the step of isolating one or more bacterial colonies.

13. The method of claim 12, wherein the one or more bacterial colonies are identified, wherein the identifying comprises performing a polymerase chain reaction (PCR).

14. The method of claim 12, wherein the one or more bacterial colonies are contacted with one or more antimicrobial compounds.

15. The method of claim 1, wherein the sample has undergone comminuting prior to the treatment to remove immune cell components.

16. The method of claim 15, wherein the comminuting is performed in a comminuting container containing comminuting media.

17. The method of claim 16, wherein the comminuting media comprises beads, shards, particles, fragments, or filaments.

18. The method of claim 16, wherein the comminuting media is formed out of glass, metal, plastic, ceramic, or any combination thereof.

* * * * *